United States Patent [19]

Pittet et al.

[11] Patent Number: 4,501,904
[45] Date of Patent: Feb. 26, 1985

[54] METHYL SUBSTITUTED 2-(2,6-DIMETHYL-1,5-HEPTADIENYL)-1,3-DITHIOLANES

[75] Inventors: Alan O. Pittet, Atlantic Highlands; Thomas F. Courtney, Jr., Oakhurst; Ranya Muralidhara, Fair Haven, all of N.J.

[73] Assignee: International Flavors & Fragrances Inc., New York, N.Y.

[21] Appl. No.: 533,666

[22] Filed: Sep. 19, 1983

[51] Int. Cl.³ .......................................... C07D 339/06
[52] U.S. Cl. ..................................... 549/35; 426/536
[58] Field of Search ................................... 549/35, 30

[56] References Cited

U.S. PATENT DOCUMENTS 4,374,998  2/1983  Boden ................................. 549/30

Primary Examiner—Henry R. Jiles
Assistant Examiner—J. G. Mullins
Attorney, Agent, or Firm—Arthur L. Liberman

[57] ABSTRACT

Described are methyl substituted 2-(2,6-dimethyl-1,5-heptadienyl)-1,3-dithiolanes defined according to the structure:

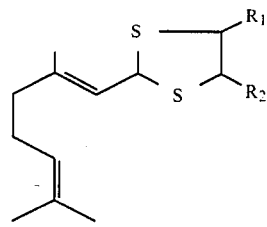

wherein $R_1$ and $R_2$ are the same or different and each represents methyl or hydrogen with the proviso that at least one of $R_1$ and $R_2$ is methyl and uses thereof in augmenting or enhancing the aroma or taste of foodstuffs.

3 Claims, 4 Drawing Figures

FIG. I

GLC PROFILE FOR EXAMPLE I, FRACTION 3.

GLC PROFILE FOR EXAMPLE II FRACTION 3.

NMR SPECTRUM FOR FRACTION 2 OF EXAMPLE II.

FIG. 4

NMR SPECTRUM FOR FRACTION 2 OF EXAMPLE II.

METHYL SUBSTITUTED 2-(2,6-DIMETHYL-1,5-HEPTADIENYL)-1,3-DITHIOLANES

BACKGROUND OF THE INVENTION

This invention provides methyl substituted 2-(2,6-dimethyl-1,5-heptadienyl)-1,3-dithiolanes defined according to the generic structure:

wherein $R_1$ and $R_2$ are the same or different and each represents methyl or hydrogen with the proviso that at least one of $R_1$ and $R_2$ is methyl and uses thereof in augmenting or enhancing the aroma or taste of foodstuffs.

Artifical flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characterists and uncertainty as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavoring development in many foods is not understood. This is notable in products having cooked liver, liverwurst, and rare liver aromas and cooked liver, liverwurst, fatty and rare liver tastes with hydrolyzed vegetable protein-like aftertastes.

Reproduction of cooked liver, liverwurst and rare liver aromas and cooked liver, liverwurst, rare liver and fatty tastes with hydrolyzed vegetable protein aftertastes has been the subject of a long and continuous search by those engaged in the production of foodstuffs. The severe shortage of foods, especially protein foods, in many parts of the world has given rise to the need for utilizing non-meat sources of proteins and making such proteins as palatable and as meat-like as possible. Hence, materials which will closely simulate or exactly reproduce flavor and aroma of liverwurst are required. Furthermore, meat flavors have been enhanced previously by the use of such materials as monosodium glutamate. In many diets, sodium is not desired. In many other diets, monosodium glutamate is not desired. Therefore a need has arisen for a monosodium glutamate replacer.

Moreover, there are a great many meat containing or meat based foods presently distributed in a preserved form. Examples of such substances are condensed soups, dry soup mixes, dry meat, freeze dried or lyophilized meats, packaged gravies and the like. While these products contain meat or meat extracts, the fragrance, taste and other organoleptic factors are very often impaired by the processing operation and it is desirable to supplement or enhance the flavors of these preserved with versatile materials which have cooked liver, liverwurst, and/or rare liver aromas and cooked liver, liverwurst, and/or rare liver and/or fatty tastes with hydrolyzed vegetable protein aftertastes.

Furthermore, there is a need for pet foods (e.g. dog foods and cat foods) which have cooked liver, liverwurst, and rare liver aromas and cooked liver, liverwurst, rare liver and fatty tastes with hydrolyzed vegetable protein-like aftertastes. There are great many pet foods presently distributed in a preserved form. Examples of such are dry meat, freeze dried or lyophilized meats, packaged gravies and the like. While these products contain meat or meat extracts, they also contain additional proteinaceous materials and the fragrance, taste and other organoleptic factors are very often impaired by the processing operation and by the presence of selected proteinaceous materials. It is thus desirable to supplement or enhance the flavors of these pet foods which are preserved with versatile materials which have cooked liver, liverwurst, and rare liver aromas and cooked liver, liverwurst, fatty and rare liver tastes with hydrolyzed vegetable protein-like aftertastes.

Alkanes having 3-methylthio moieties are known in the prior art, for example, that disclosed in Chem. Abstracts, Volume 96, No. 103327y having the structure:

This abstract is of Tetrahedron Letters, Vol. 22, number 42, pages 4159–4162, 1981, (Title: "Thiosulfonium Ions. Methylthiolation of 3-methylthio-1-butene and cis- and trans-1-methylthio-2-butene": Kim and Caserio).

Chem. Abstracts, Vol. 96:20080m which is an abstract of Fischer, Liebigs Ann. Chem., 1981 (10), 1899–1902 discloses the compound having the structure:

wherein n is 2, 3 or 4 but does not disclose its organoleptic utilities.

Chem. Abstracts, Vol. 84:164792v, (abstract of German Offenlegungsschrift No. 2,530,273) discloses the compound having the structure:

but does not disclose its organoleptic utilities.

U.S. Pat. No. 4,153,442 issued on May 8, 1979; U.S. Pat. No. 4,224,051 issued on Sept. 23, 1980; and U.S. Pat. No. 4,101,307 issued on June 18, 1978 each discloses plant growth regulating materials compounds defined according to the generic structure:

in which
X and Y which may be the same or different and represent oxygen, sulphur or a radical N-B where B is hydrogen, a lower alkyl radical containing 1 to 4 carbon atoms, an optionally substituted aryl radical or an optionally substituted acyl radical containing from 1 to 4 carbon atoms;
R and R' which may be the same or different and represent a lower alkyl radical containing from 1 to 4 carbon atoms or an acyl or amido radical containing from 1 to 4 carbon atoms; in addition they may form with a cycle corresponding to the formula in which
$R_1$, $R_2$, $R_3$ and $R_4$ which may be the same or different and represent hydrogen, an alkyl radical containing from 1 to 4 carbon atoms and optionally substituted by a halogen, the radicals $NO_2$, hydroxy or alkoxy containing from 1 to 4 carbon atoms;
A represents either a single bond or an alkylene chain containing from 1 to 4 carbon atoms optionally interrupted by an oxygen atom or a group N-B' where B' represents hydrogen, an optionally halogenated or hydroxylated alkyl group, an acyl group, the hydrocarbon portion of these radicals containing from 1 to 4 carbon atoms, or a cycle having in common with the preceding cycle 1 to 2 carbon atoms and containing from 3 to 6 carbon atoms, from 0 to 2 oxygen atoms and/or a group N-B, or a cycle corresponding to the formula Included in this generic structure is the genus defined according to the structure:

Nagao, et al, Tetrahedron Letters No. 34, pages 3167–3168 (1979) discloses the genus of compounds defined according to the structure:

in a synthetic route to yield certain ketones. In this genus R may be methyl, ethyl, propyl, butyl, tolyl, tolyl methoxy, allyl or phenyl.

Nothing in the prior art discloses the methyl substituted 2-(2,6-dimethyl-1,5-heptadienyl)-1,3-dithiolanes of our invention or its organoleptic uses however.

THE INVENTION

The present invention provides novel methyl substituted 2-(2,6-dimethyl-1,5-heptadienyl)-1,3-dithiolanes useful for augmenting or enhancing the aroma or taste of foodstuffs, said methyl substituted 2-(2,6-dimethyl-1,5-heptadienyl)-1,3-dithiolanes being defined according to the structure:

wherein $R_1$ and $R_2$ are the same or different and each represents methyl or hydrogen with the proviso that at least one of $R_1$ and $R_2$ is methyl as well as methods for augmenting or enhancing or modifying the organoleptic properties, e.g. the taste and aroma, of said foodstuffs.

The methyl substituted 2-(2,6-dimethyl-1,5-heptadienyl)-1,3-dithiolanes of our invention augment or enhance liverwurst, and liver flavored foodstuffs and pet foods. The methyl substituted 2-(2,6-dimethyl-1,5-heptadienyl)-1,3-dithiolanes of our invention provide cooked liver, liverwurst, and rare meat aromas and cooked liver, liverwurst, fatty and rare meat tastes with hydrolyzed vegetable protein-like aftertastes.

The methyl substituted 2-(2,6-dimethyl-1,5-heptadienyl)-1,3-dithiolanes of our invention having the structure:

wherein $R_1$ and $R_2$ are the same or different and each represents methyl or hydrogen with the proviso that at least one of $R_1$ and $R_2$ is methyl may be produced by means of reacting an alpha,beta-dithiol defined according to the structure:

wherein $R_1$ and $R_2$ are each the same or different and each represents methyl with the proviso that at least one of $R_1$ or $R_2$ is methyl with an aldehyde defined according to the structure:

in the presence of a protonic acid catalyst such as para-toluenesulfonic acid, xylene sulfonic acid, methane sulfonic acid, phosphoric acid and concentrated sulfuric acid. The reaction takes place in the presence of a solvent having a boiling point such that the reaction can proceed in a reasonable period of time, e.g. 1–12 hours at atmospheric pressure or pressures somewhat greater than atmospheric pressure (up to about 10 atmospheres). The reaction temperature may vary from between about 70° C. up to about 140° C. Reaction temperatures greater than 140° C. give rise to unnecessary breakdown of reaction product. Reaction temperatures lower than 70° C. give rise to too long a period of time of reaction. The solvents utilized must be inert to the reaction product as well as inert to the reactants. The solvent utilized must also have a boiling point of between 70° C. and 140° C. since the reaction is to take place under reflux conditions. The reaction solvent must also be capable of being completely removed from the product on distillation in view of the fact that the reaction products are used as food flavors for internal consumption. Accordingly, suitable solvents are, for example, cyclohexane, cyclopentane, cyclooctane, 1-methylcyclohexane, 1,2-dimethylcyclohexane, 1,2,4-trimethylcyclohexane, 2-ethyltetrahydrofuran, 2,5-dimethyltetrahydrofuran and the like.

Examples of the products of our invention and their organoleptic properties are as follows:

TABLE 1

| Structure of Compound | Organoleptic Properties |
| --- | --- |
| (structure: dithiolane with 2,6-dimethyl-1,5-heptadienyl substituent) | A cooked liver, and liverwurst aroma and a cooked liver, liverwurst and fatty taste with hydrolyzed vegetable protein aftertaste at 2 ppm causing this compound to be useful in liverwurst, dog food and cat food flavors. |
| (structure: isomeric dithiolane with 2,6-dimethyl-1,5-heptadienyl substituent) | A rare liver aroma and taste at 2 ppm causing this substance to be useful for knockwurst, dog food and cat food food flavored foodstuffs. |

At the end of the reaction as stated supra, the reaction product is extracted from the reaction mass or the reaction mass is washed, for example, with saturated sodium chloride. The reaction product is then distilled preferably by means of vacuum distillation.

Thus, the methyl substituted 2-(2,6-dimethyl-1,5-heptadienyl)-1,3-dithiolanes produced according to our invention can be used to alter, vary fortify, modify, enhance or otherwise improve the organoleptic properties, including flavor and/or aroma, of a wide variety of materials which are ingested, consumed or otherwise organoleptically sensed.

The term "alter" in its various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

Such methyl substituted 2-(2,6-dimethyl-1,5-heptadienyl)-1,3-dithiolanes of our invention are accordingly useful in flavoring compositions. Flavoring compositions are hereintaken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the methyl substituted 2-(2,6-dimethyl-1,5-heptadienyl)-1,3-dithiolanes according to this invention are used in a food flavoring composition, they can be combined with conventional flavoring materials or adjuvants. Such coingredients or flavoring adjuvants are well known in the art for such use and have been extensively described in the literature. Apart from the requirement that any such adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers.

Examples of preferred co-flavoring adjuvants are:
Methyl thiazole alcohol (4-methyl-5-betahydroxyethyl thiazole);
2-Methyl butanethiol;
4-Mercapto-2-butanone;
3-Mercapto-2-pentanone;
1-Mercapto-2-propanone;
Benzaldehyde;
Furfural;
Furfural alcohol;
2-Mercapto propionic acid;
Alkyl pyrazine;
Methyl pyrazine;
2-Ethyl-3-methyl pyrazine;
Tetramethyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Monopotassium glutamate;
Sulphur-containing amino acids, e.g. cysteine;
Hydrolyzed vegetable protein;
2-Methylfuran-3-thiol;
2-Methyldihydrofuran-3-thiol;
2,5-dimethylfuran-3-thiol;
Hydrolyzed fish protein; and
Tetramethyl pyrazine.

The methyl substituted 2-(2,6-dimethyl-1,5-heptadienyl)-1,3-dithiolanes or the compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carrageenan, other gums and the like. The methyl substituted 2-(2,6-dimethyl-1,5-heptadienyl)-1,3-dithiolanes according to this invention can be incorporated with the carriers by conventional means such as spray-drying, drum drying and the like.

Such carriers can also include materials for coacervating the methyl substituted 2-(2,6-dimethyl-1,5-heptadienyl)-1,3-dithiolanes (and other flavoring ingredients, as present) to provide encapsulated products. When the carrier is an emulsion, the flavoring composition can also contain emulsifiers such as mono- and diglycerides or fatty acids and the like. With these carriers or vehicles, the desired physical form of the composition can be prepared.

The quantity of methyl substituted 2-(2,6-dimethyl-1,5-heptadienyl)-1,3-dithiolanes utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subject; and the preconsumption treatment, such as baking, frying, and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate composition contain from about 0.1 parts per million up to about 250 parts per million of methyl substituted 2-(2,6-dimethyl-1,5-heptadienyl)-1,3-dithiolanes or mixtures thereof. More particularly, in food compositions it is desirable to use from about 0.1 to 100 parts per million for enhancing flavors and in certain preferred embodiments of the invention, from about 0.1 to about 10 parts per million of the methyl substituted 2-(2,6-dimethyl-1,5-heptadienyl)-1,3-dithiolanes are included to add positive flavors to the finished product.

The amount of methyl substituted 2-(2,6-dimethyl-1,5-heptadienyl)-1,3-dithiolanes or mixtures thereof of our invention to be utilized in flavoring compositions can be varied over a wide range depending upon the particular quality to be added to the foodstuff. Thus, amounts of one or more derivatives according to the present invention of from about 0.5 ppm up to 80 or 90% of the total flavoring composition can be incorporated in such compositions. It is generally found to be desirable to include from about 1 ppm up to about 0.1% of the methyl substituted 2-(2,6-dimethyl-1,5-heptadienyl)-1,3-dithiolanes in such compositions.

The following examples are given to illustrate embodiments of the invention as it is preferred to practice it. It will be understood that these examples are illustrative and the invention is not to be considered restricted thereto except as indicated in the appended claims.

All parts, proportions, percentages and ratios used herein are by weight unless otherwise indicated.

EXAMPLE I

PREPARATION OF 2-(2,6-DIMETHYL-1,5-HEPTADIENYL)-4,5-DIMETHYL-1,3-DITHIOLANE

Reaction:

Into a 100 ml reaction flask equipped with spin bar, reflux condenser, heating mantle and hot plate with magnetic stirring apparatus, is placed 0.5 grams para-toluenesulfonic acid, 5.0 ml cyclohexane and 6.1 grams (0.05 moles) of 2,3-butanedithiol. Over a period of 30 minutes with stirring is added to the reaction mass 7.6 grams (0.05 moles) of citral having the structure:

After the citral is added, the reaction mass is heated to reflux and refluxed (with removal of water of reaction) over a period of 9 hours. At the end of the 9 hour period, the reaction mass is cooled and transferred to a separatory funnel. The reaction mass is then washed with one 50 ml portion of saturated sodium chloride solution and then dried over anhydrous sodium sulfate, filtered and distilled on a Microvigreux column yielding the following fractions:

| Fraction Number | Vapor Temp. (°C.) | Liquid Temp. (°C.) | Vacuum mm/Hg. |
|---|---|---|---|
| 1 | 119 | 142 | 2 |
| 2 | 120 | 145 | 2 |
| 3 | 105 | 150 | 2 |

Figure 1:
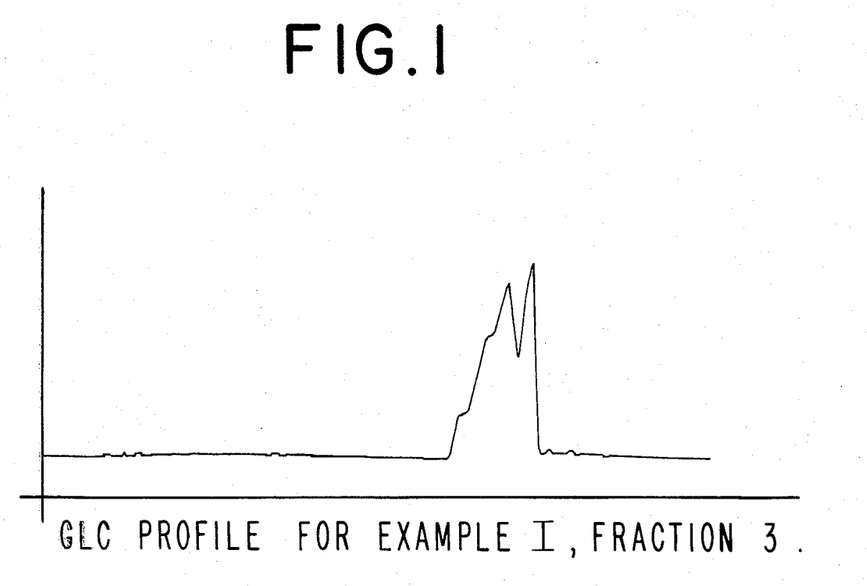
FIG. 1 is the GLC profile for fraction 3 of the distillation product of the reaction product of Example I containing the compound having the structure.

FIG. 1 is the GLC profile for fraction 3 of the foregoing distillation (conditions: SE-30, 10'×0.125" column programmed at 100°–220° C. at 8° C. per minute).

Figure 2:
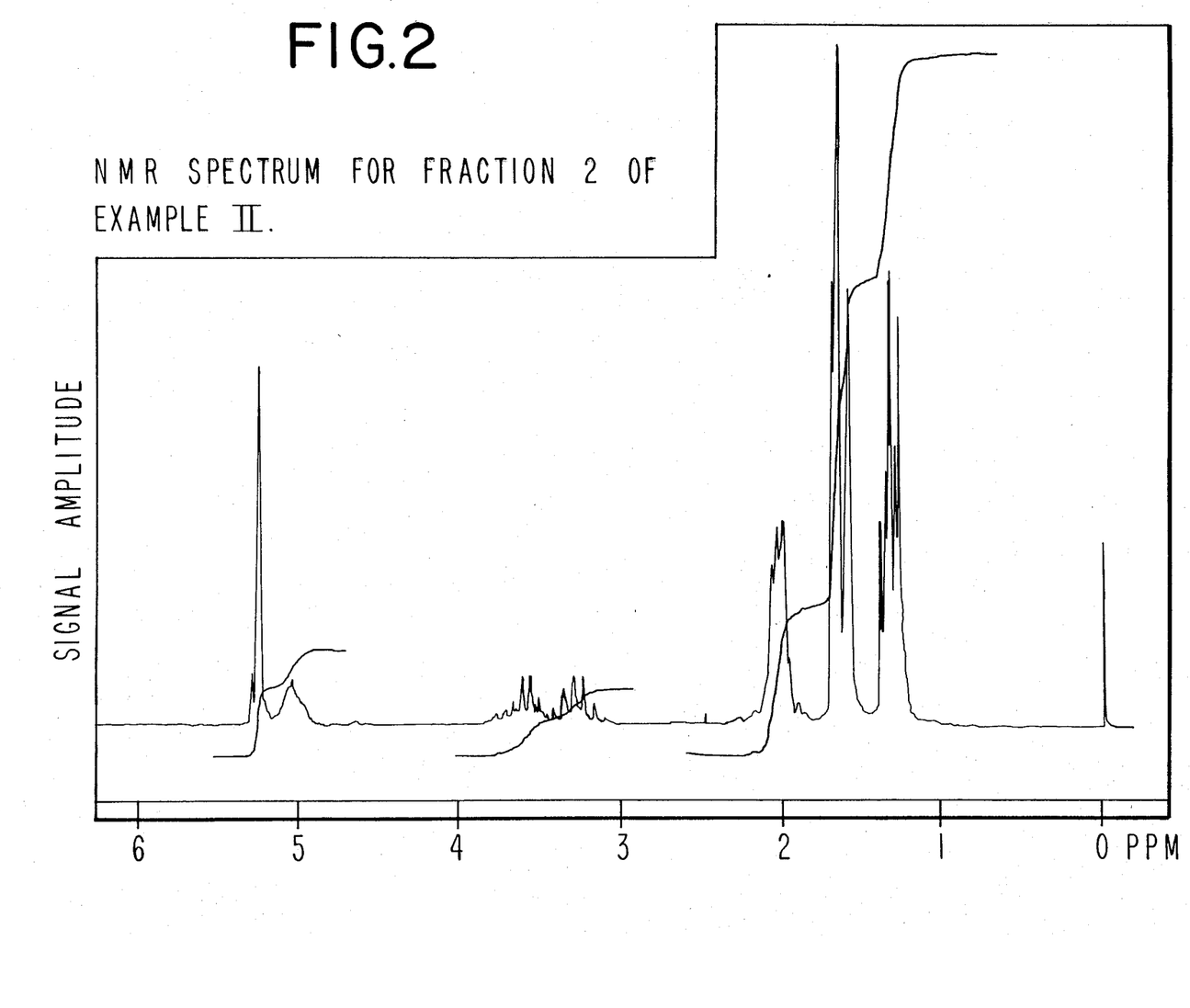
FIG. 2 is the NMR spectrum for fraction 2 of the distillation product of the reaction product of Example I containing the compound having the structure.

FIG. 2 is the NMR spectrum for fraction 2 of the foregoing distillation containing the compound having the structure:

The resulting compound has an intense cooked liver and liverwurst aroma and an intense cooked liver, liverwurst and fatty taste with hydrolyzed vegetable protein-like aftertaste at 2 ppm.

EXAMPLE II

PREPARATION OF 2-(2,6-DIMETHYL-1,5-HEPTADIENYL)-4-METHYL-1,3-DITHIOLANE

Reaction

Into a 100 ml reaction flask equipped with spin bar, reflux condenser, heating mantle and hot plate with magnetic stirring apparatus is placed 0.5 grams para-toluenesulfonic acid, 5.0 ml cyclohexane and 5.4 grams (0.05 moles) of 1,2-propanedithiol. 7.6 grams (0.05 moles) of citral is then added to the reaction mass over a period of 30 minutes. After the addition of the citral, the reaction mass is heated to reflux and refluxed for a period of 10 hours while removing water of reaction. After the 10 hour reflux period, the reaction mass is cooled and transferred to a separatory funnel. The reaction mass is then washed with one 50 ml portion of saturated sodium chloride solution followed by drying over anhydrous sodium sulfate and filtration. The resulting filtrate is distilled on a Microvigreux column yielding the following fractions:

| Fraction Number | Vapor Temp. (°C.) | Liquid Temp. (°C.) | Vacuum mm/Hg. |
|---|---|---|---|
| 1 | 110 | 130 | 2 |
| 2 | 115 | 132 | 2 |
| 3 | 115 | 133 | 2 |
| 4 | 100 | 135 | 2 |

Figure 3:
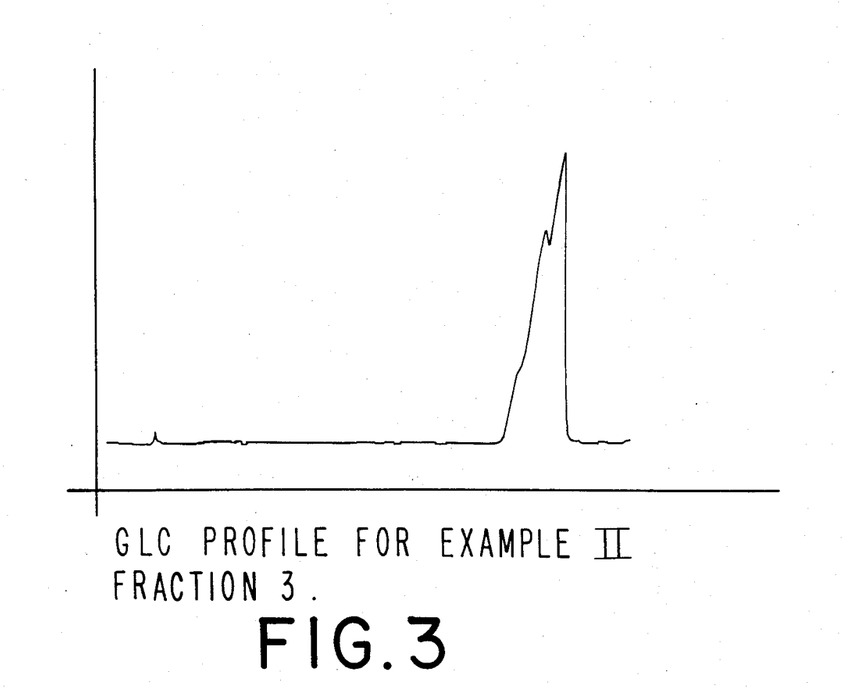
FIG. 3 is the GLC profile for fraction 3 of the distillation product of the reaction product of Example II containing the compound having the structure.
Figure 4:
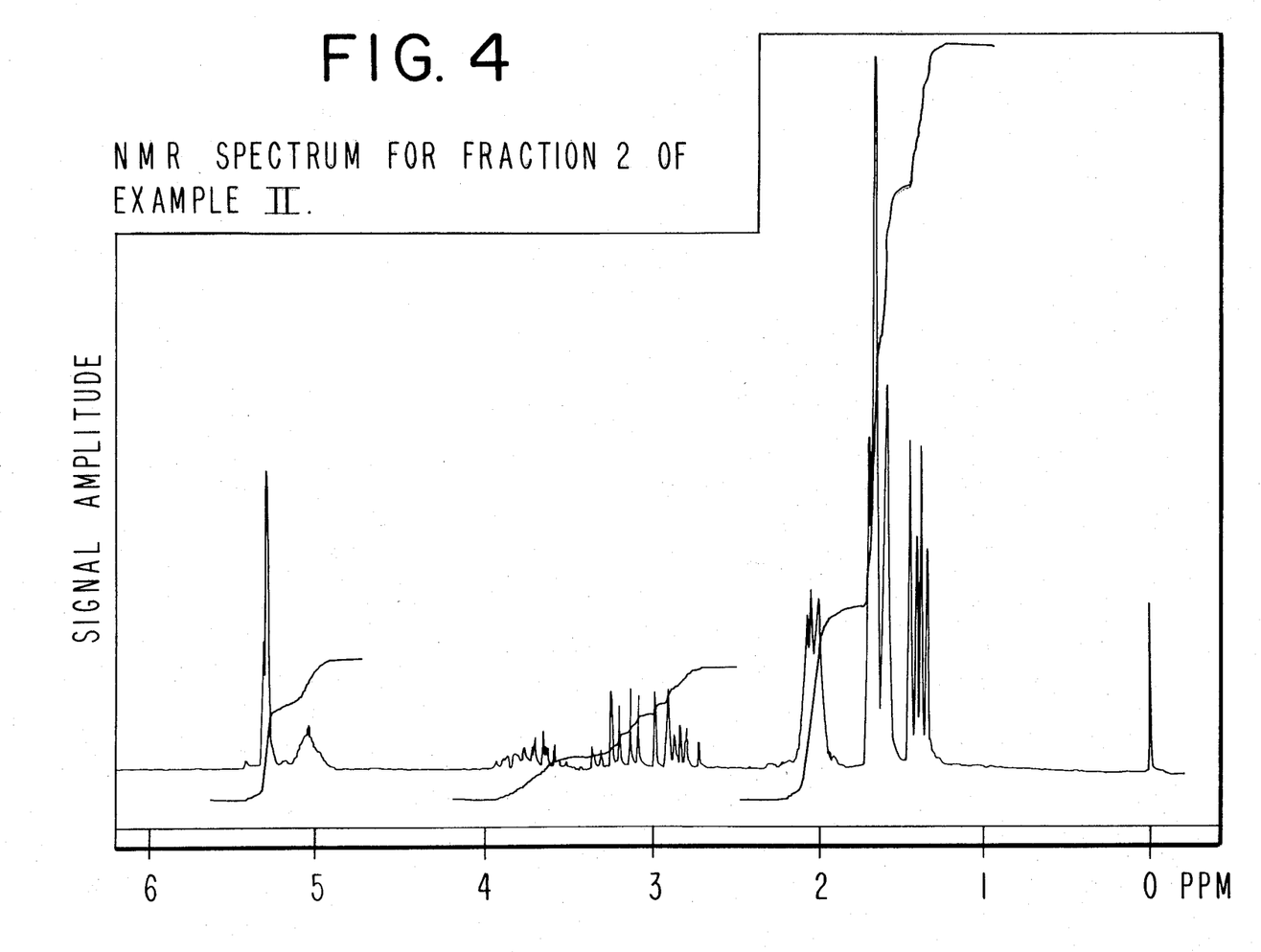
FIG. 4 is the NMR spectrum for fraction 2 of the distillation product of the reaction product of Example II containing the compound having the structure.

FIG. 3 is the GLC profile for fraction 3 of the foregoing distillation containing the compound having the structure:

FIG. 4 is the NMR spectrum for fraction 2 of the foregoing distillation containing the compound having the structure:

The resulting product has an intense, rare-liver aroma and taste at 2 ppm.

EXAMPLE III

The compound having the structure:

prepared according to Example I is dissolved in propylene glycol to provide a 0.1% solution. The solution in the amount of 0.9 grams is added to 7.3 grams of a soup base consisting of:

| Ingredient | Parts by Weight |
|---|---|
| Fine ground sodium chloride | 35.5 |
| Hydrolyzed vegetable protein | 27.5 |
| Monosodium glutamate | 18.0 |
| Sucrose | 11.0 |
| Beef fat | 5.5 |
| Sethness caramel color (powder B & C) | 2.7 |

The resulting mixture has a cooked liver, liverwurst, fatty and hydrolyzed vegetable protein-like, beef broth-like, aroma and taste.

EXAMPLE IV

The compound having the structure:

produced according to Example I is added to a 2% solution of Wyler's "Beef Flavored Instant Bouillon" (manufactured by Wyler Foods Division of Borden, Inc., Chicago, Ill.):

(Ingredients: salt, hydrolyzed vegetable protein, malto dextrin, sugar, beef fat, water, monosodium glutamate, flavorings, corn sugar, beef extract, caramel color, hydrogenated begetable fat and U.S. certified food color)

at the rate of 0.1 ppm. The resulting beef flavor has imparted to it intense cooked liver, livewurst, fatty and hydrolyzed vegetable protein-like nuances.

EXAMPLE V

A meat gravy is prepared containing 2 ppm by weight of the compound having the structure:

prepared according to Example II using a beef base and beef fat. The resulting beef gravy containing the compound having the structure:

is then added to mushrooms cooked using boiling water at a rate of 10 parts gravy to 100 parts cooked mushrooms. The resulting mushroom platter has an excellent natural-like, rare liver/mushroom flavor.

When the compound having the structure:

is added to this platter (which already contains the compound having the structure:

at the level of 2 ppm, an intense cooked liver and liverwurst aroma and taste is created in the platter.

EXAMPLE VI

At the level of 4 ppm to raw ground chuck is added the compound having the structure:

The resulting substance is then placed next to the ground chuck without the compound having the structure:

Both dogs and cats prefer (preference rate 80%) the ground chuck with the compound having the structure:

added thereto. The same result occurs when a 50:50 mixture of compounds having the structures:

is added to the ground chuck. The same results occur when the compound having the structure:

is added to the ground chuck.

EXAMPLE VII

When the compound having the structure:

is added at the rate of 2.0 ppm to a standard chicken frankfurter containing 50 parts by weight of chicken and 50 parts by weight of pork, in addition to chicken and pork nuances in the chicken frankfurter, there is added an intense cooked liver, and liverwurst aroma with a cooked liver, liverwurst and fatty taste with a hydrolyzed vegetable protein aftertaste to this chicken frankfurter. In general, the chicken frankfurter flavor can be described as having a chicken-like, pork-like, liverwurst-like, cooked liver-like and fatty aroma and taste profile with a hydrolyzed vegetable protein-like aftertaste.

What is claimed is:

1. A methyl substituted 2-(2,6-dimethyl-1,5-heptadienyl)-1,3-dithiolane having the structure:

wherein $R_1$ and $R_2$ are the same or different and each represents methyl or hydrogen with the proviso that at least one of $R_1$ and $R_2$ is methyl.

2. The methyl substituted 2-(2,6-dimethyl-1,5-heptadienyl)-1,3-dithiolane of claim 1 having the structure:

3. The methyl substituted 2-(2,6-dimethyl-1,5-heptadienyl)-1,3-dithiolane of claim 1 having the structure:

* * * * *